United States Patent [19]
Ohoka et al.

[11] Patent Number: 4,484,003
[45] Date of Patent: Nov. 20, 1984

[54] PREPARATION PROCESS OF β-CHLOROALANINE

[75] Inventors: Masaharu Ohoka, Yokohama; Toshio Katoh; Ryuichi Mita, both of Kawasaki; Nobuyuki Kawashima; Chojiro Higuchi, both of Kamakura; Nobuhiro Kawashima, Sagamihara; Akihiro Yamaguchi, Kamakura; Shousuke Nagai, Yokohama; Takao Takano, Fujisawa, all of Japan

[73] Assignee: Mitsui Toatsu Chemicals, Incorporated, Tokyo, Japan

[21] Appl. No.: 459,634

[22] PCT Filed: May 17, 1982

[86] PCT No.: PCT/JP82/00174
§ 371 Date: Dec. 29, 1982
§ 102(e) Date: Dec. 29, 1982

[87] PCT Pub. No.: WO82/04043
PCT Pub. Date: Nov. 25, 1982

[30] Foreign Application Priority Data
May 18, 1981 [JP] Japan ................................. 56-73521
Jul. 3, 1981 [JP] Japan ................................. 56-103165

[51] Int. Cl.$^3$ ............................................. C07C 51/363
[52] U.S. Cl. ..................................................... 562/574
[58] Field of Search ....................................... 562/574

[56] References Cited
FOREIGN PATENT DOCUMENTS
2051797A 1/1981 United Kingdom .

OTHER PUBLICATIONS
Gundermann, Chem. Ber., 93, pp. 1632-1643, (1960).

Primary Examiner—Michael L. Shippen
Attorney, Agent, or Firm—Fisher, Christen & Sabol

[57] ABSTRACT

β-Chloroalanine is prepared by reacting in an aqueous medium an aziridine-2-carboxylate with hydrogen chloride in an amount of 2.0–5.0 moles per mole of the aziridine-2-carboxyalte and causing the thus-formed β-chloroalanine to selectively crystallize out from the liquid reaction mixture. Since the solution recovered after the isolation of the crystallized β-chloroalanine still contains β-chloroalanine and by-produced α-chloro-β-alanine dissolved therein, they may be converted into an aziridine-2-carboxylate by treating them with a base to recirculate it for reuse.

4 Claims, No Drawings

PREPARATION PROCESS OF β-CHLOROALANINE

TECHNICAL FIELD

This invention relates to an improved preparation process of β-chloroalanine through a reaction of an aziridine-2-carboxylate with hydrogen chloride.

BACKGROUND ART

β-Chloroalanine is an amino acid having physiological activity and is an extremely useful compound as a synthesis intermediate not only for cystein, a sulfur-containing amino acid, but also for certain pharmaceutically valuable compounds and the like. Due to lack of industrially advantageous preparation processes, β-chloroalanine has not yet been utilized fully. Among known synthesis processes of β-chloroalanine, there may be mentioned to esterify serine, followed by chlorination and hydrolysis (J. L. Wood, and L. van Middlesworth, J. Bio. Chem., Vol. 179, Page 529, 1949); and to chlorinate and decompose a cystein derivative in an organic solvent by reacting the derivative with chlorine (H. Baganz and G. Dransch, Chem. Ber. Vol. 93, Page 782, 1960). However, these processes are not suitable for their applications in an industrial scale because both processes require very costly starting materials.

On the other hand, it has also been known to prepare β-chloroalanine by reacting sodium aziridine-2-carboxylate with hydrogen chloride (K. D. Gundermann, G. Holtmann, H. J. Rose, and H. Schulze, Chem. Ber., Vol. 93, Page 1632, 1960). The above process however requires extraordinarily excessive hydrogen chloride upon carrying out the reaction. Furthermore, in order to separate the resultant sodium chloride from a mixture of β-chloroalanine hydrochloride and α-chloro-β-alanine hydrochloride which is a by-product, it is necessary to add a large amount of ethanol to the reaction mixture to extract the intended product and by-product. It is also required to treat the thus-obtained extract of β-chloroalanine hydrochloride and α-chloro-β-alanine hydrochloride with ammonia, to add water to the thus-treated extract so as to crystallize β-chloroalanine and then to isolate same. The above process is not fully considered to be an advantageous preparation process from the industrial standpoint because, despite of the adoption of complex steps, the yield of isolated β-chloroalanine is as low as 10% and its isolation steps are extremely cumbersome.

DISCLOSURE OF THE INVENTION

An object of this invention is to provide a preparation process of β-chloroalanine through a reaction of an aziridine-2-carboxylate with hydrogen chloride, which process facilitates the isolation of β-chloroalanine in a crystalline form from the liquid reaction mixture.

Another object of this invention is to provide a preparation process of β-chloroalanine through a reaction of an aziridine-2-carboxylate with hydrogen chloride, which process permits to convert β-chloroalanine still remaining in the liquid reaction mixture after its isolation as crystalline β-chloroalanine into an aziridine-2-carboxylate.

The present inventors have found that, upon synthetically preparing β-chloroalanine and α-chloro-β-alanine through the reaction between an aziridine-2-carboxylate and hydrogen chloride, the reaction can be successfully carried out with a stoichiometric or slightly excessive amount of hydrogen chloride instead of using hydrogen chloride in an extraordinarily excessive amount with respect to aziridine-2-carboxylic acid or its salt and β-chloroalanine may be isolated by causing same to selectively and solely crystallize out from the reaction mixture.

It has also been found by the present inventors that β-chloroalanine may also be prepared from a solution recovered after isolating crystallized β-chloroalanine from the liquid reaction mixture, which solution still contains β-chloroalanine and α-chloro-β-alanine, by treating the solution with the hydroxide of an alkali metal or alkaline earth metal or ammonia under extremely mild conditions to obtain a solution containing an aziridine-2-carboxylate and then reacting the thus-obtained aziridine-2-carboxylate again as a starting material with hydrogen chloride.

The present invention has been completed on the basis of the above findings. Accordingly, this invention provides the following preparation process of β-chloroalanine:

A process for preparing β-chloroalanine through a reaction of an aziridine-2-carboxylate with hydrogen chloride, which process comprises conducting said reaction in an aqueous medium using 2.0–5.0 moles of hydrogen chloride per mole of the aziridine-2-carboxylate and then causing β-chloroalanine to selectively crystallize out from the resulting liquid reaction mixture.

An aziridine-2-carboxylate, which is to be obtained by treating the solution recovered after the separation of crystallized β-chloroalanine from the liquid reaction mixture with the hydroxide of an alkali metal or alkaline earth metal or ammonia, may be recirculated and reutilized as a starting material.

In the process according to this invention, the intended final product β-chloroalanine is allowed to precipitate directly from the reaction mixture and no special post processing or treatment is thus required for its separation from the by-product. Accordingly, pure β-chloroalanine can be readily isolated through filtration in an industrial scale. Moreover, unrecovered β-chloroalanine still remaining in a dissolved form in the reaction mixture as well as the by-product, α-chloro-β-alanine, may be converted into an aziridine-2-carboxylate through a simple reaction, thereby obtaining the aziridine-2-carboxylate in a high concentration. It may then be recirculated and reutilized as a starting material. As has been described above, the preparation process according to this invention has many merits and is thus extremely valuable for the industry.

BEST MODE OF CARRYING OUT THE INVENTION

In the present process, an aziridine-2-carboxylate is employed as a starting material. Among suitable aziridine-2-carboxylates, may be mentioned its alkali metal salts such as the lithium, sodium and potassium salts, its alkaline earth metal salts such as the magnesium and calcium salts, and its ammonium salt.

Such an aziridine-2-carboxylate may be readily synthesized with a high yield by reacting α-chloro-β-aminopropionitrile hydrochloride or α-amino-β-chloropropionitrile hydrochloride with the hydroxide of an alkali metal such as lithium, sodium or potassium or an alkaline earth metal such as magnesium or calcium in an amount of 3–3.5 moles per mole of the former reactant.

The preparation process according to this invention generally uses conc. hydrochloric acid as the hydrogen chloride. No problem will arise when hydrogen chloride gas is blown into the reaction system if necessary. Hydrogen chloride is employed in an amount of 2.0–2.5 moles per mole of an alkali metal salt or the ammonium salt of aziridine-2-carboxylic acid to be used. A preferred molar ratio of hydrogen chloride to the latter reactant ranges 2.05–2.3. On the other hand, hydrogen chloride may be used in an amount of 4.0–5.0 moles, and preferably, 4.05–4.8 moles per mole of an alkaline earth metal salt of aziridine-2-carboxylic acid. The reaction yield will be low and the yield of isolated $\beta$-chloroalanine will correspondingly be poor when hydrogen chloride is employed in any amounts below 2.0 moles per mole of an alkali metal salt or the ammonium salt of aziridine-2-carboxylic acid or in any amounts less than 4.0 moles per mole of an alkaline earth metal salt of aziridine-2-carboxylic acid. It is, on the other hand, undesirable to employ hydrogen chloride in any amounts exceeding 2.5 moles per mole of an alkali metal salt or the ammonium salt of aziridine-2-carboxylic acid or in any amounts beyond 5.0 moles per mole of an alkaline earth metal salt of aziridine-2-carboxylic acid, since such excess hydrogen chloride will make the yield of isolated $\beta$-chloroalanine considerably low.

In the present preparation process, the reaction between an aziridine-2-carboxylate and hydrogen chloride is carried out in an aqueous medium. A water is a particularly preferred aqueous reaction medium. The amount of a solvent to be used upon carrying out the reaction shall not be limited to any specific one. Thus, the reaction may still be carried out successfully without encountering any problems even if $\beta$-chloroalanine is contained in the reaction medium at a concentration level either below the lower limit of its crystallizable concentration range or above the upper limit of the same crystallizable concentration range. The crystallizable concentration range of $\beta$-chloroalanine will be discussed later in this specification. However, it is necessary to adjust the concentration of a liquid reaction mixture through its dilution or concentration for crystallizing $\beta$-chloroalanine out from the liquid reaction mixture if its concentration in the liquid reaction mixture is outside its crystallizable concentration range. Therefore, in view of the crystallization conditions of $\beta$-chloroalanine, it is generally preferred to use the aqueous reaction medium in such an amount that the concentration of resulting $\beta$-chloroalanine falls within such a concentration range as to permit the selective crystallization of $\beta$-chloroalanine.

The reaction may be carried out at 0°–100° C., and preferably, 0°–50° C. The reaction time varies depending on various reaction parameters but generally ranges from 1 to 50 hours, and more preferably, from 2 to 25 hours. The end of the reaction can be quickly determined with ease by using analytical means such as high-speed liquid chromatography.

Then, $\beta$-chloroalanine is caused to crystallize out selectively from the thus obtained liquid reaction mixture. As conditions required to allow the selective crystallization of $\beta$-chloroalanine, there are the total concentration of $\beta$-chloroalanine and $\alpha$-chloro-$\beta$-alanine in the liquid reaction mixture and the crystallization temperature.

Thus, it is necessary for the crystallization of $\beta$-chloroalanine from the liquid reaction mixture to, first of all, adjust the total concentration of $\beta$-chloroalanine and $\beta$-chloro-$\alpha$-alanine in the liquid reaction mixture. Suitable total concentration range varies in accordance with the type of aziridine-2-carboxylate to be used. The following total concentration ranges are to be given for their corresponding starting materials:

(1) 10–47 wt. %, and preferably, 27–46 wt. % when lithium aziridine-2-carboxylate is employed;

(2) 8–28 wt. %, and preferably, 15–27 wt. % when sodium aziridine-2-carboxylate is employed;

(3) 8–25 wt. %, and preferably, 12–24 wt. % when potassium aziridine-2-carboxylate is employed;

(4) 10–41 wt. %, and preferably, 26–40 wt. % when magnesium aziridine-2-carboxylate is employed;

(5) 10–46 wt. %, and preferably, 20–45 wt. % when calcium aziridine-2-carboxylate is employed; and (6) 8–31 wt. %, and preferably, 18–30 wt. % when ammonium aziridine-2-carboxylate is employed.

Accordingly, it is unnecessary to adjust the total concentration of $\beta$-chloroalanine and $\alpha$-chloro-$\beta$-alanine when the ring-opening and chlorination reaction is conducted within the crystallizable concentration range for the aziridine-2-carboxylate used for the reaction. However, where the ring-opening and chlorination reaction is carried out outside its corresponding crystallizable concentration range, it is necessary to concentrate or dilute the resultant liquid reaction mixture so as to adjust its total concentration of $\beta$-chloroalanine and $\alpha$-chloro-$\beta$-alanine within the crystallizable concentration range corresponding to the aziridine-2-carboxylate employed for the reaction. If the crystallization of $\beta$-chloroalanine is carried out below the lower limit of the crystallizable concentration range for each aziridine-2-carboxylate, $\beta$-chloroalanine is isolated with a lowered yield. On the other hand, any total concentrations of $\beta$-chloroalanine and $\alpha$-chloro-$\beta$-alanine beyond the upper limit of the crystallizable concentration range for each aziridine-2-carboxylate will lead to an inclusion of the by-product ($\alpha$-chloro-$\beta$-alanine) and resulting inorganic salt in $\beta$-chloroalanine. Thus, such total concentrations are not preferred.

$\beta$-Chloroalanine is then caused to crystallize out, normally at a temperature of $-30°$ C. to $+40°$ C., and preferably, at a temperature of $-20°$ C. to $+30°$ C. from the liquid reaction mixture which has been adjusted beforehand in concentration as mentioned above. Any temperatures below the lower limit induce an inclusion of the by-product and the like in $\beta$-chloroalanine. If the crystallization temperature exceeds the above upper limit, the yield of isolated $\beta$-chloroalanine will be lowered considerably. Thus, any temperatures outside the former temperature range are not preferred. There is no particular limitation vested to the time required for the crystallization. The crystallization may be completed in 0.5–80 hours, and normally, in 1–50 hours within the above temperature ranges. The completion of crystallization can be quickly and readily determined by analytical means such as high-speed liquid chromatography.

Since $\beta$-chloroalanine is selectively separated as precipitate from the liquid reaction mixture in accordance with the method mentioned above, it can be readily isolated by virtue of filtration. Even if the thus-obtained crystalline $\beta$-chloroalanine contains a trace amount of impurities adhered thereon, such impurities can be removed by washing the crystalline $\beta$-chloroalanine with a small amount of cold water and/or an organic solvent miscible with water. Such an organic solvent may be selected, for example, from alcohols such as methanol, ethanol, n-propanol, isopropanol and tert.-butanol, acetones, dioxane, tetrahydrofuran, etc.

According to the second aspect of this invention, β-chloroalanine may also be prepared from a solution recovered after isolating the crystallized β-chloroalanine from the liquid reaction mixture, by subjecting β-chloroalanine and α-chloro-β-alanine dissolved in the thus-recovered solution to a ring-closing reaction with a base to obtain an aziridine-2-carboxylate and then using the thus-obtained aziridine-2-carboxylate again as a starting material.

By the term "recovered solution" as used in the above reaction route is meant a filtrate resulted from the collection of crystallized β-chloroalanine through filtration or a mixture of the above filtrate and a washing liquid occurred from washing the thus-collected crystalline β-chloroalanine.

Since the recovered solution still contains a saturating amount of β-chloroalanine and the by-product, α-chloro-β-alanine dissolved therein, they may be subjected to a ring-closing reaction by treating them with the hydroxide of an alkali metal or alkaline earth metal or ammonia, thereby obtaining a solution which contains an aziridine-2-carboxylate. As the hydroxide of an alkali metal or alkaline earth metal usable here, it is possible to use such a base as lithium hydroxide, sodium hydroxide, potassium hydroxide, magnesium hydroxide, calcium hydroxide or the like. Such a base is employed in such an amount that it is consumed to neutralize hydrogen chloride present in the recovered solution and of two equivalent weights or more with respect to β-chloroalanine and α-chloro-β-alanine contained in the recovered solution. There is no particular upper limit as to the amount of the base to be used, but it is not advantageous from the economical standpoint to use it in a considerably excessive amount. Generally speaking, it is sufficient when the base is used within a range up to 5 equivalent weights.

The above reaction may be carried out in either water or a water-containing organic solvent. Namely, the recovered solution permits the above reaction to take place when its solvent is either water or a mixture of water and a water-miscible organic solvent. As water-miscible organic solvents, may be mentioned for example alcohols such as methanol, ethanol, n-propanol, isopropanol, tert-butanol, cellosolve, methylcellosolve and the like, acetones, dioxane, tetrahydrofuran, etc. Thus, as mentioned above, the above reaction may still be carried out in a recovered solution containing a washing liquid which has occurred from washing crystalline β-chloroalanine collected through filtration with an organic solvent.

When using both water and an organic solvent together for the reaction, they may be used in any proportions. A water-containing organic solvent may be used in an amount 3-200 times, and preferably 5-100 times the total amount of β-chloroalanine and α-chloro-β-alanine contained in the recovered solution. The reaction temperature may range from 0° C. to 100° C., and preferably, from 20° C. to 80° C. The reaction time varies depending on various conditions of the reaction. However, the reaction may be brought to completion in 0.5–50 hours, and normally, in 2.0–30 hours. The end of the reaction may be readily determined in a short time period by thin-layer chromatography. After causing water and/or organic solvent to evaporate under the atmospheric pressure or reduced pressures and, if necessary, filtering off the inorganic salt which deposits upon concentration of the reaction mixture, the resultant aziridine-2-carboxylate can be obtained in the form of an aqueous solution.

The thus-obtained aqueous solution of the aziridine-2-carboxylate may be reacted as a starting material of the present process with hydrogen chloride under the above-mentioned reaction conditions after adjusting its concentration by concentrating or diluting same or adding a fresh supply of the aziridine-2-carboxylate to same, thereby also preparing β-chloroalanine.

As has been described above, β-chloroalanine and α-chloro-β-alanine contained in a filtrate which has been obtained after isolating crystalline β-chloroalanine can be utilized effectively. By repeating the above process according to the second aspect of this invention, β-chloroalanine can be prepared efficiently and extremely advantageously from the industrial viewpoint.

The process of this invention will be described in the following examples.

EXAMPLE 1

To 84 g of 35% hydrochloric acid stirred under ice-cooling, was added over 2 hours 117.9 g of a 32% aqueous solution of sodium aziridine-2-carboxylate. The resulting mixture was allowed to undergo a reaction for 22 hours at room temperature, followed by an ice-cooling of the liquid reaction mixture for 5 hours. Deposited β-chloroalanine was collected through filtration and then washed with a small amount of methanol to give 17 g of β-chloroalanine (yield: 39% based on sodium aziridine-2-carboxylate). Melting point: 142° C. (decomposed). From the result of an NMR spectrum analysis (solvent: $D_2O$) on the thus-obtained crystalline β-chloroalanine, it was confirmed that β-chloroalanine was free of α-chloro-β-alanine.

EXAMPLE 2

To 23 g of 35% hydrochloric acid stirred under ice-cooling, was added over 1 hour 9.3 g of lithium aziridine-2-carboxylate. The resultant mixture was allowed to undergo a reaction for 6 hours at room temperature. The resultant liquid reaction mixture was ice-cooled for 5 hours and the crystalline deposit was collected through filtration and washed with a small amount of ethanol, thereby obtaining 5.2 g of β-chloroalanine. Its molar yield was 42% based on the lithium aziridine-2-carboxylate.

EXAMPLE 3

To 94 g of 35% hydrochloric acid stirred under ice-cooling, was added over 1 hour 194 g of a 28% aqueous solution of potassium aziridine-2-carboxylate. The resultant mixture was allowed to undergo a reaction for 10 hours at room temperature, followed by an ice-cooling of the liquid reaction mixture for 4 hours. Deposited crystals were filtered off and washed with a small amount of methanol to give 20.7 g of β-chloroalanine. Its molar yield was 39% based on the potassium aziridine-2-carboxylate.

EXAMPLE 4

To 43.8 g of 35% hydrochloric acid stirred under ice-cooling, was added over 2 hours 21.2 g of calcium aziridine-2-carboxylate, followed by a reaction for 20 hours at room temperature. The liquid reaction mixture was ice-cooled for 5 hours and the resultant β-chloroalanine deposit was collected through filtration and washed with a small amount of methanol, resulting in the provision of 9.1 g of β-chloroalanine(yield: 37% based on the calcium aziridine-2-carboxylate).

EXAMPLE 5

To 22.9 g of 35% hydrochloric acid stirred under ice-cooling, was added over 2 hours 27.9 g of a 3.7% aqueous solution of ammonium aziridine-2-carboxylate. The resultant mixture was allowed to undergo a reaction for 23 hours at room temperature. The liquid reaction mixture was ice-cooled for 4 hours and the resulting β-chloroalanine deposit was collected through filtration and washed with a small amount of methanol to give 4.5 g of β-chloroalanine(yield: 36% on the basis of the ammonium aziridine-2-carboxylate).

EXAMPLE 6

To 84 g of 35% hydrochloric acid stirred under ice-cooling, was added over 2 hours 117.9 g of a 32% aqueous solution of sodium aziridine-2-carboxylate. Thereafter, a reaction was caused to take place for 22 hours at room temperature. The liquid reaction mixture was then ice-cooled for 5 hours. The resultant β-chloroalanine deposit was collected through filtration and then washed with a small amount of methanol, thereby obtaining 17 g of β-chloroalanine(yield: 39% based on the sodium aziridine-2-carboxylate; melting point: 142° C.-decomposed).

Then, the filtrate and the washing liquid were combined with 340 g of a 6% aqueous solution of sodium hydroxide and allowed to react at 45° C. for 6 hours. The resulting solution was concentrated by causing methanol and water to evaporate under reduced pressures. Deposited inorganic salt was then filtered off, thereby obtaining 55 g of a 32% aqueous solution of sodium aziridine-2-carboxylate. This solution was thereafter added to 375 g of 35% hydrochloric acid which had been ice-cooled and, after following the same procedure as mentioned above, 7.6 g of β-chloroalanine was obtained. The overall yield of β-chloroalanine reached 24.6 g, which was equivalent to a yield of 51% based on the sodium aziridine-2-carboxylate employed at the beginning.

EXAMPLE 7

To 94 g of 35% hydrochloric acid stirred under ice-cooling, was added over 1 hour 194 g of a 28% aqueous solution of potassium aziridine-2-carboxylate. The resultant mixture was caused to undergo a reaction for 10 hours at room temperature, followed by ice-cooling the liquid reaction mixture for 4 hours. The resultant crystalline deposit was collected through filtration and washed with a small amount of methanol to give 20.7 g of β-chloroalanine.

To 277 g of a mixture of the resultant filtrate and washing liquid, was added 361 g of a 10% aqueous solution of potassium hydroxide. They are allowed to react at 50° C. for 5 hours. The resulting solution was concentrated by driving off methanol and water under reduced pressures. Upon removal of the resultant deposit of the inorganic salt through filtration, 84 g of a 31% aqueous solution of potassium aziridine-2-carboxylate was obtained. This solution was added to 60 g of 35% hydrochloric acid stirred under ice-cooling and, after following the same procedure as mentioned above, 8.9 g of β-chloroalanine was resulted. The overall yield of β-chloroalanine was 29.6 g, which was equivalent to a yield of 56% based on the potassium aziridine-2-carboxylate charged at the beginning.

EXAMPLE 8

To 22.9 g of 35% hydrochloric acid stirred under ice-cooling, was added over 2 hours 27.9 g of a 37% aqueous solution of ammonium aziridine-2-carboxylate. Then, the resultant mixture was allowed to undergo a reaction at room temperature for 23 hours. The liquid reaction mixture was then ice-cooled for 5 hours and the resultant β-chloroalanine deposit was filtered off and washed with a small amount of methanol, thereby obtaining 4.5 g of β-chloroalanine. Thereafter, 51.3 g of a mixture of the filtrate and washing methanol was combined with 29 g of a 10% aqueous ammonia solution and reacted at room temperature for 30 hours. The solvents were caused to evaporate under reduced pressures and, upon removal of the resultant deposit of the inorganic salt, 18 g of a 30% aqueous solution of ammonium aziridine-2-carboxylate was obtained. It was then treated in the same manner as in the above, using 16 g of 35% hydrochloric acid to give 1.8 g of β-chloroalanine. The overall yield of β-chloroalanine was 6.3 g, which was equivalent to a yield of 50% based on the ammonium aziridine-2-carboxylate charged at the beginning of this experiment.

EXAMPLE 9

To 50 g of 35% hydrochloric acid stirred under ice-cooling, was added 21.2 g of calcium aziridine-2-carboxylate. Then, the resultant mixture was allowed to react at room temperature for 6 hours. The liquid reaction mixture was ice-cooled for 5 hours and the resultant crystalline deposit was collected through filtration. It was then washed with a small amount of methanol, thereby obtaining 8.9 g of β-chloroalanine.

Thereafter, the filtrate and the washing liquid were added to 280 g of a 6% suspension of calcium hydroxide and allowed to undergo a reaction at 60° C. for 7 hours. The resultant solution was subjected to filtration so as to remove any excessive calcium hydroxide. The resultant filtrate was concentrated under reduced pressures to give 32 g of a 33% aqueous solution of calcium aziridine-2-carboxylate. This solution was then added to 27 g of ice-cooled 35% hydrochloric acid. Following the same procedure as mentioned above, 4.1 g of β-chloroalanine was obtained. The overall yield of β-chloroalanine was 13 g, which was equivalent to a yield of 50% based on the calcium aziridine-2-carboxylate used at the beginning of this experiment.

EXAMPLE 10

To 168 g of 35% hydrochloric acid which had been heated to 40° C., was added over 2 hours 236 g of a 32% aqueous solution of sodium aziridine-2-carboxylate. Then, the resultant mixture was reacted at 40°-45° C. for 1 hour and the liquid reaction mixture was cooled at −16° C. for 2 hours. The resulting β-chloroalanine deposit was collected through filtration and washed with a small amount of isopropanol, thereby obtaining 39 g of β-chloroalanine(yield: 45% based on the sodium aziridine-2-carboxylate).

Then, the filtrate and the washing liquid were combined with 388 g of a 10% aqueous solution of sodium hydroxide and reacted at 45° C. for 4 hours. The thus-obtained solution was concentrated by causing isopropanol and water to evaporate under reduced pressures.

By filtering off the resultant deposit of the inorganic salt, 105 g of a 32% aqueous solution of sodium aziridine-2-carboxylate was obtained. This solution was thereafter added to 85 g of 35% hydrochloric acid and caused to react with the latter in the same manner as mentioned above, thereby obtaining 18 g of β-chloroalanine. The overall yield of β-chloroalanine was 55 g, which was equivalent to a yield of 64% based on the sodium aziridine-2-carboxylate used at the beginning of this experiment.

EXAMPLE 11

The procedure of Example 6 was repeated. From the second experiment, a fresh supply of the aqueous solution of sodium aziridine-2-carboxylate was incorporated to adjust its concentration and quantity to the same levels as used in the first experiment. Results are shown in Table 1.

TABLE 1

| Experiment No. | Recovery rate of AZ—Na (%)* | Yield of β-chloro-alanine (%)** |
|---|---|---|
| 1st | 48.8 | 39 |
| 2nd | 47.5 | 38.5 |
| 3rd | 48.0 | 38.6 |
| 4th | 48.2 | 37.9 |
| 5th | 47.0 | 38.0 |

Note:
*Expressed in terms of a recovery rate (%) when recovered as a 32% aqueous solution of sodium aziridine-2-carboxylate.

Recovery rate (%) = $\frac{\text{Weight recovered}}{\text{Weight charged}} \times 100$

**Indicates the yield in each experiment.

We claim:

1. Process for preparing β-chloroalanine through a reaction of an aziridine-2-carboxylate with hydrogen chloride, which comprises conducting said reaction in an aqueous medium using, per mole of the aziridine-2-carboxylate:
    (i) 2.0 to 2.5 moles of hydrogen chloride when the aziridine-2-carboxylate is alkali metal or ammonium aziridine-2-carboxylate; and
    (ii) 4.0 to 5.0 moles of hydrogen chloride when the aziridine-2-carboxylate is alkaline earth metal aziridine-2-carboxylate, adjusting the total concentration of β-chloroalanine and α-chloro-β-alanine in the resulting liquid reaction mixture:
    (a) 10 to 47 wt. percent when the aziridine-2-carboxylate is lithium aziridine-2-carboxylate;
    (b) 8 to 28 wt. percent when the aziridine-2-carboxylate is sodium aziridine-2-carboxylate;
    (c) 8 to 25 wt. percent when the aziridine-2-carboxylate is potassium aziridine-2-carboxylate;
    (d) 10 to 41 wt. percent when the aziridine-2-carboxylate is magnesium aziridine-2-carboxylate;
    (e) 10 to 46 wt. percent when the aziridine-2-carboxylate is calcium aziridine-2-carboxylate; and
    (f) 8 to 31 wt. percent when the aziridine-2-carboxylate is ammonium aziridine-2-carboxylate, and then causing β-chloroalanine to selectively crystallize out at −30° to +40° C. from the resulting liquid mixture.

2. The process as claimed in claim 1 wherein the reaction between the aziridine-2-carboxylate and hydrogen chloride is conducted at 0° to 100° C.

3. Process for preparing β-chloroalanine, which comprises reacting in an aqueous medium an aziridine-2-carboxylate with hydrogen chloride in an amount, per mole of the aziridine-2-carboxylate, of:
    (i) 2.0 to 2.5 moles of hydrogen chloride when the aziridine-2-carboxylate is alkali metal or ammonium aziridine-2-carboxylate; and
    (ii) 4.0 to 5.0 moles of hydrogen chloride when the aziridine-2-carboxylate is alkaline earth metal aziridine-2-carboxylate, adjusting the total concentration of β-chloroalanine and α-chloro-β-alanine in the resulting liquid reaction mixture to;
    (a) 10 to 47 wt. percent when the aziridine-2-carboxylate is lithium aziridine-2-carboxylate;
    (b) 8 to 28 wt. percent when the aziridine-2-carboxylate is sodium aziridine-2-carboxylate;
    (d) 10 to 41 wt. percent when the aziridine-2-carboxylate is magnesium aziridine-2-carboxylate;
    (e) 10 to 46 wt. percent when the aziridine-2-carboxylate is calcium aziridine-2-carboxylate; and
    (f) 8 to 31 wt. percent when the aziridine-2-carboxylate is ammonium aziridine-2-carboxylate;
then causing α-chloroalanine to selectively crystallize out at −30° to +40° from the resulting liquid mixture so as to isolate same, treating the recovered solution, which contains β-chloroalanine and α-chloro-β-alanine, with the hydroxide of an alkali metal or alkaline earth metal or ammonia, and recirculating and re-utilizing the thus-obtained aziridine-2-carboxylate as a starting material.

4. The process as claimed in claim 3 wherein the recovered solution is treated at 0° to 100° C.

* * * * *